(12) United States Patent
Wessjohann et al.

(10) Patent No.: US 9,371,358 B2
(45) Date of Patent: Jun. 21, 2016

(54) TUBULYSIN ANALOGUES

(75) Inventors: Ludger A. Wessjohann, Saale (DE); Orlando Pando Morejon, Saale (DE)

(73) Assignee: Leibniz-Institut Fur Pflanzenbiochemie, Halle (Saale) (DE)

( * ) Notice: Subject to any disclaimer, the term of this patent is extended or adjusted under 35 U.S.C. 154(b) by 0 days.

(21) Appl. No.: 13/811,212

(22) PCT Filed: Jul. 18, 2011

(86) PCT No.: PCT/EP2011/003588
§ 371 (c)(1),
(2), (4) Date: Mar. 26, 2013

(87) PCT Pub. No.: WO2012/010287
PCT Pub. Date: Jan. 26, 2012

(65) Prior Publication Data
US 2013/0217638 A1    Aug. 22, 2013

(30) Foreign Application Priority Data
Jul. 19, 2010 (EP) ..................................... 10007468

(51) Int. Cl.
*C07K 5/02* (2006.01)
*C07K 5/078* (2006.01)

(52) U.S. Cl.
CPC . *C07K 5/02* (2013.01); *C07K 5/021* (2013.01); *C07K 5/06173* (2013.01)

(58) Field of Classification Search
CPC .............. A61K 31/165; A61K 31/497; A61K 49/0052; C07D 487/04; C07K 5/021; C07K 5/02
See application file for complete search history.

(56) References Cited

U.S. PATENT DOCUMENTS

| 4,442,029 A | 4/1984 | Marquarding et al. |
| 2005/0239713 A1 | 10/2005 | Domling et al. |
| 2010/0048490 A1 | 2/2010 | Vlahov et al. |

FOREIGN PATENT DOCUMENTS

| DE | 19638870 A1 | 3/1998 |
| DE | 10008089 A1 | 10/2001 |
| DE | 10230872 A1 | 1/2004 |
| DE | 10230874 A1 | 1/2004 |
| DE | 10230875 A1 | 1/2004 |
| DE | 10254439 A1 | 6/2004 |
| DE | 10305531 A1 | 8/2004 |
| DE | 102004030227 A1 | 1/2006 |
| EP | 1562979 A2 | 8/2005 |

(Continued)

OTHER PUBLICATIONS

Ivar Ugi. Recent progress in the chemistry of multicomponent reactions. Pure Appl. Chem. 2001. 73(1):187-191.*

(Continued)

*Primary Examiner* — Karlheinz R Skowronek
*Assistant Examiner* — Jia-Hai Lee
(74) *Attorney, Agent, or Firm* — Armstrong Teasdale LLP (57) ABSTRACT

The present invention relates to novel tubulysin compounds (tubulysin analogs) as well as pharmaceutical formulations thereof. The present invention further relates to the use of such compounds for medicinal, agricultural, biotool or cosmetic applications. In particular, the novel tubulysin analogs show a cytostatic effect and can therefore be used for the treatment of proliferative disorders. The tertiary amide moiety of the tubulysin analogs (so-called tubugis) according to the present invention is generated by an Ugi-type reaction.

13 Claims, 1 Drawing Sheet

(56) References Cited

FOREIGN PATENT DOCUMENTS

| | | |
|---|---|---|
| EP | 2028185 A1 | 2/2009 |
| JP | 2006518704 A | 8/2006 |
| WO | 2004005269 A1 | 1/2004 |
| WO | 2004005326 A2 | 1/2004 |
| WO | 2004005327 A1 | 1/2004 |
| WO | 2004046170 A2 | 6/2004 |
| WO | 2008112873 A1 | 9/2008 |
| WO | WO 2008/112873 A2 * | 9/2008 ............. A61K 47/48 |
| WO | 2008138561 A1 | 11/2008 |
| WO | 2009012958 A1 | 1/2009 |
| WO | 2009055562 A1 | 4/2009 |
| WO | WO2009/055562 A1 * | 4/2009 ............. A61K 31/445 |
| WO | 2009134279 A1 | 11/2009 |
| WO | 2010034724 A1 | 4/2010 |

OTHER PUBLICATIONS

Domling et al. Total Synthesis of Tubulysin U and V. Angew. Chem. Int. Ed. 2006, 45, 7235-7239.*

F. Sasse et al., "Tubulysins, new cytostatic peptides from myxobacteria acting on microtubuli. Production, isolation, physico-chemical and biological properties.", J. Antibiot. 2000, 53, 879-885.

H. Steinmetz at al., "Isolation, crystal and solution structure determination and biosynthesis of tubulysins—powerful inhibitors of tubulin polymerization from myxobacteria.", Angew. Chem., Int. Ed. 2004, 43, 4888-4892.

H. M. Peltier et al., "The total syntheses of tubulysin D.", J. Am. Chem. Soc. 2006, 128, 16018-16019.

O. Pando et al., "First total synthesis of tubulysin B.", Org. Lett., 2009, 11, 5567-5569.

International Preliminary Report on Patentability and Written Opinion from PCT/EP2011/003588, dated Jan. 22, 2013.

Scudiero, et al., "Evaluation of a Soluble Tetrazolium/Formazan Assay for Cell Growth and Drug Sensitivity in Culture Using Human and Other Tumor Cell Lines", Cancer Res., 1988, 48, 4827-4833.

International Search Report and Written Opinion from PCT/EP2011/003588, dated Sep. 12, 2011.

Pando, et al., "The Multiple Multicomponent Approach to Natural Product Mimics: Tubugis, N-Substituted Anticancer Peptides with Picomolar Activity", JACS, 2011, vol. 133, p. 7692-7695 and Supplementary Information.

Patterson, et al., "Design, Synthesis, and Biological Properties of Highly Potent Tubulysin D Analogues," Chem. Eur. J., 2007, vol. 13, p. 9534-9541.

Patterson, et al., "Expedient Synthesis of N-Methyl Tubulysin Analogues with High Cytotoxicity", J. Org. Chem., 2008, vol. 73, p. 4362-4369.

Shaabani et al., "A Novel Approach for the Synthesis of Aryl Amides," Tetrahedron Letters, 2007, vol. 48, p. 6137-6141.

Wu et al., "Total Synthesis of Cyclosporine: Access to N-Methylated Peptides via Isonitrile Coupling Reactions," J. Am. Chem. Soc., 2010, vol. 132, p. 4098-4100.

Pallai, P. et al., "Extended Retro-Inverso Analogs of Somatostatin," Biopolymers, 1983, 22 (12), 2523-2538.

Raghavan B. et al., "Cytotoxic Simplified Tubulysin Analogues," Journal of Medicinal Chemistry, 2008, 51 (6), 1530-1533.

Office action from Japanese Patent Application 2013-520001, dated Jul. 14, 2015 (English translation).

* cited by examiner

TUBULYSIN ANALOGUES

CROSS-REFERENCE TO RELATED APPLICATIONS

This application is a U.S. National Phase patent application of International Application Serial Number PCT/EP2011/003588, filed on Jul. 18, 2011, which is hereby incorporated by reference in its entirety, and which claims the benefit of European Patent Application Number 10007468.1, filed on Jul. 19, 2010, which is hereby incorporated by reference in its entirety.

FIELD OF THE DISCLOSURE

The present invention relates to novel tubulysin compounds (tubulysin analogues) as well as pharmaceutical formulations thereof. The present invention further relates to the use of such compounds for medicinal, agricultural, biotool or cosmetic applications. In particular, the novel tubulysin analogues show a cytostatic effect and can therefore be used for the treatment of proliferative disorders. The tertiary amide moiety of the tubulysin analogues (so-called tubugis) according to the present invention is generated by an Ugi-type reaction.

BACKGROUND OF THE DISCLOSURE

Tubulysins, a novel class of antimitotic tetrapeptides that strongly inhibit microtubule polymerization, were first isolated from myxobacterial cultures (F. Sasse et al. J. Antibiot. 2000, 53, 879). Growth inhibition factors ($GI_{50}$) ranging from nanomolar to picomolar concentrations, exceeding by 20- to 1000-fold that of well known chemotherapeutic agents like Taxol or Vinblastine, and a high cytotoxic activity on multi-drug-resistant cell lines make tubulysins exciting leads for the development of novel anticancer drugs (H. Steinmetz at al., Angew. Chem., Int. Ed. 2004, 43, 4888).

Formula (I)

Tubulysin A, $R^1$ = OH, $R^2$ = $CH_2CH(CH_3)_2$
Tubulysin D, $R^1$ = H, $R^2$ = $CH_2CH(CH_3)_2$ Tubulysin D of formula (I) is the most potent member of this family of cytotoxins. Structurally, tubulysins are comprised of four amino acids which constitute the basic structure of this tetrapeptide as represented in formula (I): at the C-terminus tubuphenylalanine (Tup) or tubutyrosine (Tut), the complex tubuvaline (Tuv) as the central core, L-isoleucine (Ile), and the hydrophobic D-N-methyl pipecolic acid (Mep) as the N-terminal amino acid. An unusual amide N,O-acetal ester functionality which makes the middle part of the molecule extremely crowded, is also present. In general, natural tubulysins carrying this functionality have the greatest cytotoxic activity.

From the synthetic point of view this rare chemical motif represents a major challenge, and only few groups have succeeded on its introduction during the total synthesis of tubulysins (H. M. Peltier et al. J. Am. Chem. Soc. 2006, 128, 16019; and O. Pando et al. Org. Lett., 2009, 11, 5567). To date, several methods for the synthesis of tubulysins (DE 100 08 089, DE 102 54 439, DE 196 38 870, EP 1 562 979, EP 2 028 185, US 2005/0239713, DE 102 30 872, WO 2004/046170, WO 2009/055562) and analogues and/or conjugates of tubulysin (DE 102 30 874, DE 102 30 875, DE 103 05 531, DE 10 2004 030 227, US 2010/0048490, WO 2004/005269, WO 2004/005326, WO 2004/005327, WO 2008/138561, WO 2009/012958, WO 2009/134279, WO 2010/034724) have been proposed.

However, due to synthetic challenges, these methods generally provide the tubulysins and/or their analogues in relatively small amounts. In addition, extremely toxic electrophilic reagents have to be used during the preparation of the tubulysins and/or their analogues. Moreover, analogues of tubulysin which elude the N,O-acetal functionality, commonly exhibit inferior cytotoxic activities when compared with e.g. tubulysin D.

BRIEF SUMMARY OF THE DISCLOSURE

Accordingly, an object of the present invention is to provide a new generation of highly cytotoxic tubulysin compounds which can be easily synthesized in high yield, concurrently avoiding the use of highly toxic electrophilic reagents. The new compounds should be capable of forming conjugates to biomolecules for the target-oriented delivery, and/or to molecular moieties that can improve solubility, penetration, release or selectivity (e.g. tissue selectivity).

The solution to the above objectives is provided by the embodiments as characterized in the claims.

DETAILED DESCRIPTION OF THE DISCLOSURE

In particular, the present invention provides tubulysin analogues having a tertiary tetrapeptide structure (so-called tubugis) of the general formula (II):

(II)

wherein:

W is a group selected from $OR^{13}$ or $NR^{14}R^{15}$,

X is a substituted five- or six-membered aromatic (arylene) or heteroaromatic ring (hetero-arylene), preferably thiazole or oxazole, Y is H, —$CH_2$—, NH, NMe, a sulfur atom or oxygen atom, preferably an oxygen atom, Z is a group selected from $OR^{16}$, $NR^{17}R^{18}$ or:

$R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$, $R^{18}$, $R^{20}$, $R^{21}$, $R^{23}$, $R^{24}$ and $R^{25}$ each independently represents H, a substituted or unsubstituted alkyl, a substituted or unsubstituted cycloalkyl, a substituted or unsubstituted aryl, a substituted or unsubstituted heteroaryl, a substituted or unsubstituted heteroalkyl, and where $R^1$ and $R^3$ or $R^1$ and $R^2$ may be linked to form together with the nitrogen atom a five-membered pyrrolidine ring or a six-membered piperidine ring, $R^{12}$ is H, an acyl group (C(O)R), a substituted or unsubstituted alkyl, a substituted or unsubstituted cycloalkyl, a substituted or unsubstituted aryl, with R being a substituted or unsubstituted alkyl, a substituted or unsubstituted cycloalkyl, or a substituted or unsubstituted aryl, $R^{19}$ represents H, halogen, nitro, amine, monoalkylamine or dialkylamine group, hydroxyl, alkyloxy, a substituted or unsubstituted alkyl, a substituted or unsubstituted cycloalkyl, a substituted or unsubstituted aryl, a substituted or unsubstituted heteroaryl, a substituted or unsubstituted heteroalkyl; in positions 2 and/or 3 and/or 4, and/or 5, and/or 6, or in any combination, $R^{22}$ represents OH, $NH_2$, alkyloxy, alkylamino or dialkylamino group, or a linker, V is a sulfur or oxygen atom, —$CH_2$—, NH or NH-alkyl group, and pharmaceutical acceptable salts, hydrates, solvates, prodrugs, metabolites, stereoisomers, stereoisomeric mixtures and polymorphs thereof.

The present invention also relates to the tubugis of the formula (II) conjugated to biomolecules for the target-oriented delivery. A biomolecule is defined as a peptide, functional protein, enzyme, antigen, antibody, (oligo)saccharide, (poly)saccharide, nucleic acid, hormone or hormone receptor binder, or vitamin. The conjugation can be mediated by a linker.

The present invention also relates to the tubugis of the formula (II) conjugated to molecular moieties that can improve solubility, penetration, detection, release or selectivity (e.g. tissue selectivity) of the tubugis. Such moieties are for example polyethyleneglycols, polyamines, polyguanidines, dyes, or receptor ligands, or polymers which are preferentially captured by specific tissues due to their size and form and/or which allow a defined release. The conjugation can be mediated by a linker.

In an embodiment of the present invention, such a linker may comprise an aliphatic chain —$(CH_2)_n$— with n being an integer of from 1 to 12, an oligoethylene glycol —(O—$CH_2$—$CH_2)_n$— with n being an integer of from 1 to 12, a synthetic poly(ethylene glycol), or a phenylene ring, optionally substituted with one or more substituents selected from the group consisting of F, Cl, Br, I, $NO_2$, $SO_3H$, CN, OH, COOH, a $O_{1-8}$ alkyl group and a $C_{1-6}$ aryl group, or combinations thereof. It is particularly preferred that the linker group contains a synthetic polymer selected from the group consisting of poly(ethylene glycol) (PEG), monomethoxy PEG (mPEG), polyglycerol (PG), poly(ethylene imine) (PEI) and N-(2-hydroxypropyl)methacrylamide (HPMA) copolymers, and combinations thereof. It is particularly preferable that the linker group comprises PEG having a mass e.g. ranging from 1,000 to 50,000 Da. It is more preferred that the PEG has a mass in the range of from 2,000 to 20,000 Da. Examples of such linker groups can be derived from commercially available protected mercapto derivatives of PEG of the following structure SuOOC—$CH_2$—$CH_2$-PEG-$CH_2$—$CH_2$—S-Trt. This group can be converted into a unit for the linker group having the structure —OOC—$CH_2$—$CH_2$-PEG-$CH_2$—$CH_2$—S—.

Linkers can also contain at any chemically suitable position within the chain a cleavable moiety like a disulfide (reductive or basic-nucleophilic cleavage), an acid or base sensitive ester group (acidic or basic/nucleophilic cleavage, respectively) or an acetal or heteroacetal moiety (acidic cleavage or also oxidative cleavage for O/S and S/S acetals), whereby the cleavable moieties may be designed in a way that they respond specifically to certain pH or enzymes that promote such cleavage in vivo.

Accordingly, in the course of the present invention, polyethyleneglycols can serve as linker as well as molecular moieties that can improve solubility, penetration, release or selectivity (e.g. tissue selectivity) of the tubugis.

Moreover, the present invention provides the use of the above defined tubugis and their formulations and/or conjugates for pharmaceutical, medicinal, agricultural, biotool or cosmetic applications. In particular, the tubugis and their formulations and/or conjugates of the present invention can be used in applications which require the killing of cells of any type. Preferably, the tubugis and their formulations and/or conjugates are used to inhibit abnormal cell growth, particularly for the treatment of proliferative disorders like cancer.

Figure 1:
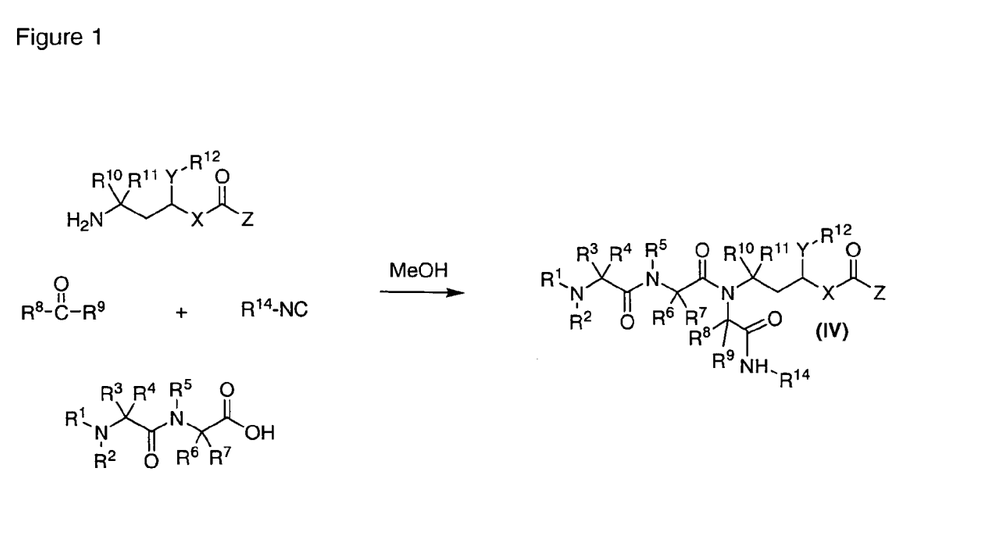
FIG. 1 depicts a method of producing compounds having the general formula (IV) by a Ugi-type reaction for the generation of the tertiary amine bond.

The present invention is also directed to a method of producing compounds having the general formula (IV) by an Ugi-type reaction for the generation of the tertiary amide bond (see FIG. 1)

(IV)

wherein

X is a substituted five- or six-membered aromatic (arylene) or heteroaromatic ring (hetero-arylene), preferably thiazole or oxazole, Y is H, —CH$_2$—, NH, NMe, a sulfur atom or oxygen atom, preferably an oxygen atom, Z is a group selected from OR$^{16}$, NR$^{17}$R$^{18}$ or:

$R^1$, $R^2$, $R^3$, $R^4$, $R^5$, $R^6$, $R^7$, $R^8$, $R^9$, $R^{10}$, $R^{11}$, $R^{17}$, $R^{18}$, $R^{20}$, $R^{21}$, $R^{23}$, $R^{24}$ and $R^{25}$ each independently represents H, a substituted or unsubstituted alkyl, a substituted or unsubstituted cycloalkyl, a substituted or unsubstituted aryl, a substituted or unsubstituted heteroaryl, a substituted or unsubstituted heteroalkyl, and where $R^1$ and $R^3$ may be linked to form together with the nitrogen atom a five-membered pyrrolidine ring or a six-membered piperidine ring, $R^{12}$ is H, an acyl group (C(O)R), a substituted or unsubstituted alkyl, a substituted or unsubstituted cycloalkyl, a substituted or unsubstituted aryl, with R being a substituted or unsubstituted alkyl, a substituted or unsubstituted cycloalkyl, or a substituted or unsubstituted aryl, $R^{14}$, $R^{16}$ is a substituted or unsubstituted alkyl, a substituted or unsubstituted cycloalkyl, a substituted or unsubstituted aryl, a substituted or unsubstituted heteroaryl, a substituted or unsubstituted heteroalkyl, or a usual O-protective group, $R^{19}$ represents H, halogen, nitro, amine, monoalkylamine or dialkylamine group, hydroxyl, alkyloxy, a substituted or unsubstituted alkyl, a substituted or unsubstituted cycloalkyl, a substituted or unsubstituted aryl, a substituted or unsubstituted heteroaryl, a substituted or unsubstituted heteroalkyl; in positions 2 and/or 3 and/or 4, and/or 5, and/or 6; or in any combination, $R^{22}$ represents NH$_2$, alkyloxy, alkylamino or dialkylamino group, or a linker,

V is a sulfur or oxygen atom, —CH$_2$—, NH or NH-alkyl group.

Figure 2:
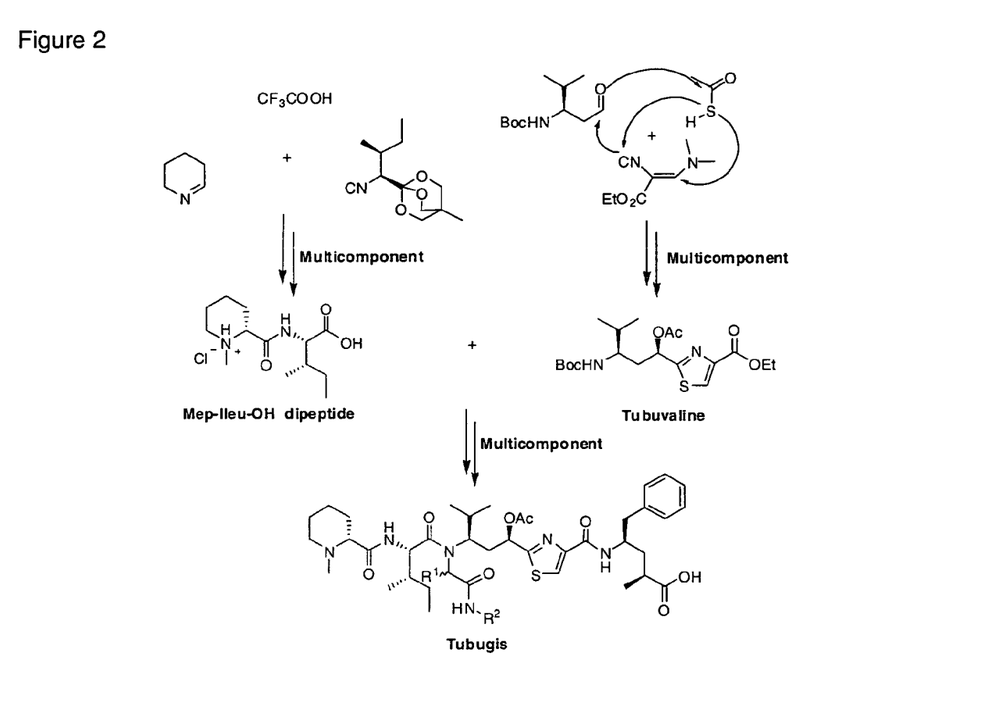
FIG. 2 depicts an exemplified sequential multiple multi-component reaction on the synthesis of tubugis according to the present disclosure.

According to the present invention it has been found that the introduction of a peptide backbone instead of the labile N,O-acetal functionality of natural tubulysins as shown in formula (I) by means of an Ugi-type reaction as the key step surprisingly leads to a novel generation of tertiary tetrapeptides (tubugis) with retention of the cytotoxic activity, and improved bioavailability. Additionally, tubugis exhibit better hydrolytic stability than tubulysins. The Ugi four-components reaction (Ugi-4CR) is the one-pot condensation of a primary amine, an oxo component, a carboxylic acid, and an isocyanide to afford an N-substituted dipeptide backbone. The Ugi-4CR provides a very straightforward method for the introduction of both molecular diversity and complexity arising from the possibility of using different carboxy, oxo, isocyano or amino component in a highly atom efficient one-pot procedure merely generating water as a byproduct as represented in FIG. 1. For the sake of further illustration, FIG. 2 shows an exemplified sequential multiple multicomponent reaction on the synthesis of tubugis according to the present invention.

According to the present invention, tubugis of the general formula (II) wherein Y is an oxygen atom and X is a thiazole or oxazole, particularly a thiazole, are preferred. Tubugi compounds according to the present invention where $R^1$ and $R^3$ in formula (II) are linked to form together with the nitrogen atom a piperidine moiety are even more preferred. In another embodiment, Z is preferably tubuphenylalanyl (Tup) or tubutyrosyl (Tut), more preferably Z is tubuphenylalanyl (Tup). In a further embodiment, W is preferably $NR^{14}R^{15}$. In an even more preferred embodiment according to the present invention, in said formula (II) X is a thiazole moiety or oxazole, $R^1$ and $R^3$ are linked to form a piperidine moiety, Z is tubuphenylalanyl (Tup), and W is $NR^{14}R^{15}$.

According to the present invention, compounds having the following formula (III) are particularly preferred:

(III)

wherein:
R' is H or a methyl group,
$R^{14}$, $R^{15}$ and Z are defined as above, wherein Z being tubuphenylalanyl (Tup) is most preferred.

According to the present invention, the compounds A to H as given herein below are even more preferred, in particular compounds A, B and D.

A

B

C

D

E

F

G and

H

The tubugis of the general formula (II) or (III), respectively, according to the present invention represent the first example of multiple multicomponent reactions-based synthesis of natural product related compounds of this class.

The following are definitions of terms used in this specification and the claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

The term "substituted alkyl" refers to an alkyl group as defined above having one, two, or three substituents selected from the group consisting of halo (e.g. trifluoromethyl), alkenyl, substituted alkenyl, alkynyl, nitro, cyano, oxo (=O), $OR_a$, $SR_a$, (=S), $-NR_aR_b$, $-N(alkyl)_3{}^+$, $-NR_aSO_2$, $-NR_aSO_2R_c$, $-SO_2R_c$, $-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)$ $(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2$(alkyl), $C_{3-7}$cycloalkyl, phenyl, benzyl, phenylethyl, naphthyl, a four to seven membered heterocylo, or a five to six membered heteroaryl, or when attached to the same nitrogen atom may join to form a heterocyclo or heteroaryl, and $R_c$ is selected from same groups as $R_a$ and $R_b$, but is not hydrogen.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substitutents as defined above for substituted alkyl groups.

The term "cycloalkyl" includes such rings having zero, one, two, or three substituents selected from the group of substituents as given hereinabove for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. Accordingly, the term "cycloalkyl" includes cyclopropyl, cyclobutyl, cyclopentyl, cyclohexyl, cycloheptyl, and cyclooctyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" particularly refers to phenyl, biphenyl, 1-naphthyl and 2-naphthyl. The term "aryl" includes such rings having zero, one, two or three substituents selected from the group as defined above for substituted alkyl groups. A preferred aryl group is optionally-substituted phenyl.

The terms "heterocyclo" or "heterocyclic" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and the like.

The present invention will be further described in more detail with reference to examples. However, it should be understood that the present invention is by no means limited to such specific examples.

Cell Culture and Cytotoxicity:

Human prostate cancer cell line (PC-3) and human colon cancer cell line (HT-29) were obtained from the German Collection of Microorganisms. All cell lines were cultivated under conditions recommended by their respective depositors. The cytotoxicity and $GI_{50}$ determinations on both PC-3 and HT-29 cell lines were performed employing a MTT cell proliferation assay (D. A. Scudiero et al. Cancer. Res. 48, 4827-4833 (1988)). Both cell lines were kept in a RPMI 1640 medium supplemented with 10% fetal bovine serum, 1% L-alanyl-L-glutamin (200 mM), 1% penicillin/streptomycin and 1.6% hepes (1 M). For PC-3 cell lines 500 cells per well and for HT-29 cell lines 1500-2000 cells per well were seeded overnight into 96-well cell culture plates (TPP, Trasadingen, Switzerland) and exposed to serial dilutions of each inhibitor for 3 days. Formazan salt formation was measured at 490 nm using an enzyme-linked immunosorbent assay (ELISA) reader (DYNEX technologies MRX TC II). From each compound four independent replicates were prepared.

General Procedure for the Ugi-4CR Reaction:

To a solution of the free amine (0.24 mmol, 1 eq.) in MeOH (3 ml) was slowly added a suspension of the carbonyl component (0.24 mmol, 1 eq.) in MeOH (3 ml) using a syringe pump over a period of 2 h. Subsequently, the acid component (0.6 mmol, 2.5 eq.) was added, the reaction was stirred 10 min and afterward a solution of the isocyanide component (0.24 mmol, 1 eq.) in MeOH (3 ml) was added over a period of 3 h using a syringe pump. The reaction mixture was stirred for an additional 6 h and the solvent was then removed under reduced pressure. Flash column chromathography afforded compound with the formula (IV).

Preparation of Mep-Ile-OH 1b:

To a solution of the 4-methyl-2,6,7-trioxabicyclo[2.2.2]octyl (OBO)-ester of isoleucine isocyanide (225 mg, 1 mmol) in MeOH (7 ml) was added a freshly prepared ethanolic solution of $\Delta^1$-piperideine (maximum concentration 0.4 M, 20 ml). Afterwards, $CF_3COOH$ (101 µl, 1.5 mmol) was dropped and the reaction mixture was stirred for 15 h. Subsequently, an additional amount of $CF_3COOH$ (101 µl, 1.5 mmol) was added and the stirring was kept over a period of 30 min. The solvent was then removed under reduced pressure and the resulting oil was dissolved in a mixture of $THF/H_2O$ (10 ml, 4:1, v/v).

Then, a solution of NaOH (400 mg, 10 mmol) in water (15 ml) was added and the reaction mixture was stirred for 1.5 h. The reaction mixture was then treated with concentrated aqueous solution of HCl (37%) until pH=7-8 was reached. Afterwards, the basic mixture was neutralized with DOWEX 50 W×2 ($H^+$-form) resin, filtered and the solvent removed under reduced pressure. The resulting crude was used on the next step without any further purification.

The oil obtained above was dissolved in a mixture of $MeOH/H_2O$ (20 ml, 3:1, v/v). Paraformaldehyde (300 mg, 10 mmol) and 20% $Pd(OH)_2/C$ (106 mg, 0.1 mmol Pd) was added. The reaction mixture was stirred under hydrogen atmosphere over a period of 16 h and afterwards filtered over celite. The solvent was then removed under reduced pressure. The resulting mixture of diastereomers (approximately 1:1 ratio) was resolved by flash column chromatography ($CH_3COOEt/MeOH/H_2O$, 7/2/1). The two diastereomers were separately collected and the fractions were independently concentrated and filtered over a 0.22 µm RC-syringe filter. The solvent was then removed under reduced pressure. The resulting oils were placed in different flasks and each one dissolved in $THF/H_2O$ (6 ml, 1:1, v/v). Both solutions were then acidified until pH=2 with concentrated aqueous solution of HCl (37%). The stirring was kept for 5 min. Afterwards, the THF in both cases was removed under reduced pressure. The resulting aqueous solutions were extracted with n-butanol (3×3 ml). The separately collected organic fractions were dried over $Na_2SO_4$ and the solvent removed under reduced pressure. The two solids were then dried under high vacuum over a period of 2 h to afford 105 mg (0.36 mmol, 36% overall yield) of the less polar diastereomer 1a $R_f$=0.38 ($CH_3COOEt/MeOH/H_2O$, 5/4/1), and 91 mg (0.31 mmol, 31% overall yield) of the more polar diastereomer 1b $R_f$=0.17 ($CH_3COOEt/MeOH/H_2O$, 5/4/1). The unequivocal stereo chemical assignment of the diastereomers 1a and 1b was performed by comparison of their respective $R_f$ and specific optical rotation values with those of the hydrochloride salt of Mep-Ileu-OH synthesized by classical peptide coupling in four steps. No significant differences were found after a comparison of the spectra of both diastereomers. The NMR spectra proved to be pH-dependent. For the diastereomer with the natural stereochemistry 1b: $^1$H-NMR (399.9 MHz, $CD_3OD$): δ=0.92 (t, 3H, J=7.3 Hz), 0.97 (d, 3H, J=7.0 Hz), 1.26-1.36 (m, 1H), 1.43-1.54 (m, 1H), 1.63-1.99 (m, 6H), 2.12-2.16 (m, 1H), 2.83 (s, 3H), 3.16 (td, 1H, J=12.3/2.6 Hz), 3.50-3.55 (d, 1H, J=12.9 Hz), 4.03 (dd, 1H, J=11.7/2.9 Hz), 4.32 (d, 1H, J=5.3 Hz) ppm. HRMS calcd for $C_{13}H_{25}N_2O_3$ $[M+H]^+$: 257.1861. found: 257.1863.

Compound 2

To a solution of N-Boc tubuvaline ethyl ester (82 mg, 0.22 mmol) in DMF (1 ml) was added TBDSCl (83 mg, 0.55 mmol, 2.5 eq.) and imidazol (2.5 eq.) at 0° C. The reaction mixture was allowed to reach room temperature, stirred overnight and diluted with ether (3 ml). The mixture was washed with saturated aqueous $NaHCO_3$ (2×5 ml) and brine (2×5 ml). The layers were separated and the organic portion was dried over $Na_2SO_4$, filtered, and concentrated under reduced pressure until dryness. The resulting crude was dissolved in $CH_2Cl_2$ (1 ml), the solution cooled at 0° C. and TFA (0.25 ml) was added. The mixture was stirred and the evolution of the reaction was carefully monitored by TLC until the starting material was consumed (approximately in 4 h). The mixture was then concentrated under reduced pressure and the resulting oil was redissolved in $CH_2Cl_2$ (5 ml). The formed solution was washed with saturated aqueous $NaHCO_3$ (3×5 ml) and brine (3×5 ml). The layers were separated and the organic phase was dried over $Na_2SO_4$, filtered, and the solvent removed under reduced pressure. The crude material was used in the next step without further purification.

To a solution of the free amine obtained above in dry MeOH (3 ml) was slowly added a suspension of formaldehyde (7.2 mg, 0.24 mmol) in MeOH (3 ml) using a syringe pump over a period of 2 h. Subsequently, 1b (154 mg, 0.6 mmol) was added, the reaction was stirred 10 min and afterwards a solution of n-butyl isocyanide (27 µl, 0.24 mmol) in MeOH (3 ml) was added over a period of 3 h using a syringe pump. The reaction mixture was stirred for an additional 6 h and the solvent was then removed under reduced pressure. Flash column chromatography ($CH_2Cl_2/MeOH/Et_3N$, 30:1: 0.3, v/v/v) afforded 69 mg (0.091 mmol, 41% yield over the three steps) of the peptoid 2 as a yellow oil. A mixture of conformers was observed by NMR (estimated ratio 4:1). Assigned signals belong to the major conformer. $^1$H-NMR (599.8 MHz, $CDCl_3$): δ=−0.07 (s, 3H, $(CH_3)_2Si$), 0.17 (s, 3H, $(CH_3)_2Si$), 0.78 (d, 3H, J=6.6 Hz), 0.90 (d, 6H, J=7.8 Hz), 0.93 (s, 9H, $(CH_3)_3CSi$), 0.98 (t, 6H, J=6.6 Hz), 1.14 (m, 1H),

1.31-1.35 (m, 3H), 1.39 (t, 3H, J=7.8 Hz), 1.44-1.51 (m, 4H), 1.59-1.69 (m, 5H), 1.98-2.09 (m, 3H), 2.19 (s, 3H), 2.44-2.46 (m, 1H), 2.87-2.88 (m, 2H), 3.21-3.25 (m, 1H), 3.29-3.33 (m, 1H), 3.67 (d, 1H, J=17.2 Hz), 4.35-4.45 (m, 6H), 5.10 (m, 1H), 7.0 (d, 1H), 8.06 (s, 1H) ppm. HRMS calcd for $C_{37}H_{68}N_5O_6SSi$ $[M+H]^+$: 738.4654. found: 738.4658.

Compound 3

N-Boc tubuvaline ethyl ester (70 mg, 0.19 mmol) was treated with TBDSCl (72 mg, 0.48 mmol) followed by Boc deprotection and the Ugi-4CR employing formaldehyde (21 mg, 0.20 mmol), 1b (123 mg, 0.48 mmol) and isopropyl isocyanide (19 μl, 0.20 mmol) in a similar way as described for the synthesis of peptoid 2 to render 49 mg (0.068 mmol, 35% yield over the three steps) of peptoid 3 as a yellow oil after flash column chromatography ($CH_2Cl_2$/MeOH/$Et_3N$, 30:1:0.3, v/v/v). A mixture of conformers was observed by NMR (estimated ratio 2:1). Assigned signals belong to the mixture of conformers. $^1$H-NMR (599.8 MHz, $CDCl_3$): δ=−0.09 (s, 3H, $(CH_3)_2Si$), −0.08 (s, 1.5H, $(CH_3)_2Si$), 0.15 (s, 3H, $(CH_3)_2Si$), 0.17 (s, 3H, $(CH_3)_2Si$), 0.78 (d, 3H, J=6.6 Hz), 0.84-0.88 (m, 9H, J=7.8 Hz), 0.93 (s, 9H, $(CH_3)_3CSi$), 0.95 (s, 4.5H, $(CH_3)_3CSi$), 0.98 (t, 4.5H, J=6.6 Hz), 1.08 (d, 1.5H, J=6.4 Hz). 1.13-1.16 (m, 6H), 1.19 (d, 3H, J=6.4 Hz), 1.39 (t, 4.5H, J=7.2 Hz), 1.60-1.71 (m, 5H), 1.78-1.87 (m, 3H), 1.98-2.03 (m, 3H), 2.05 (s, 1.5H), 2.06-2.13 (m, 2H), 2.21 (s, 3H), 2.40-2.51 (br m, 1H), 2.85-2.93 (br m, 1H), 3.64 (d, 1.5H, J=17.4 Hz), 3.79-3.86 (br m, 0.5H), 3.93-4.0 (br m, 1H), 4.04-4.15 (m, 2.5H), 4.34-4.46 (m, 6H), 4.64 (d, 0.5H, J=9.1 Hz), 5.15 (m, 1H), 5.20 (dd, 0.5H, J=9.7/1.9 Hz), 8.07 (s, 1H), 8.11 (s, 0.5H) ppm. HRMS calcd for $C_{36}H_{66}N_5O_6SSi$ $[M+H]^+$: 724.4498. found: 724.4486.

Diastereomeric mixture 4

N-Boc tubuvaline ethyl ester (100 mg, 0.27 mmol) was treated with TBDSCl (101 mg, 0.68 mmol) followed by Boc deprotection and the Ugi-4CR employing ethanal (9 μl, 0.3 mmol), 1b (174 mg, 0.68 mmol) and n-butyl isocyanide (34 μl, 0.3 mmol) in a similar way as described for the synthesis of compound 2 to render 105 mg (0.14 mmol, 52% yield over the three steps) of the diastereomeric mixture 4 as a yellow oil after flash column chromatography. Two conformers of each diastereomer can be distinguished by NMR. Assigned signals belong to the whole mixture. $^1$H-NMR (399.9 MHz, $CDCl_3$):

δ=−0.18-0.15 (m, 21H, $(CH_3)_2Si$), 0.25 (s, 3H, $(CH_3)_2Si$), 0.81-0.95 (m, 72H), 0.96-1.17 (m, 28H), 1.22-1.42 (m, 32H), 1.48-1.90 (m, 28H), 1.92-2.09 (m, 8H), 2.16-2.19 (m, 12H), 2.22-2.48 (m, 8H), 2.81-2.94 (m, 4H), 3.0-3.11 (m, 4H), 3.18-3.34 (m, 7H), 3.40-3.51 (m, 1H), 3.82-4.01 (m, 4H), 4.07-4.13 (m, 2H), 4.20-4.42 (m, 10H), 4.46 (br s, 1H), 4.54-4.60 (br s, 1H), 4.65-4.70 (m, 2H), 4.73-4.81 (br s, 1H), 4.95-5.04 (m, 2H), 5.25-5.28 (m, 1H), 5.36-5.40 (m, 1H), 8.04-8.14 (4s, 4H) ppm. HRMS calcd for $C_{38}H_{70}N_5O_6SSi$ $[M+H]^+$: 752.4811. found: 752.4805.

General Procedure for Compounds 5, 6 and 7:

Compound 5

Silyl ether 2 (24 mg, 32.8 μmol) was dissolved in TFA/THF/$H_2O$ (2 ml, 2:2:1, v/v/v) and stirred at room temperature over 36 h. The mixture was then concentrated under reduced pressure and the resulting oil dissolved in $CH_2Cl_2$, which was distilled to azeotropically remove TFA. This procedure was repeated several times. Afterwards, the crude material was dissolved in THF/$H_2O$ (1 ml, 2:1, v/v) and LiOH (2.0 mg, 82 μmol, 2.5 eq.) was added at 0° C. The reaction mixture was allowed to reach room temperature, stirred 8 h, and acidified with aqueous 10% $NaHSO_4$ to pH 4. The mixture was diluted with EtOAc (1 ml), the layers were separated and the aqueous phase was extracted with EtOAc (3×2 ml). The combined organic phases were concentrated under reduced pressure. The resulting acid was added to a 0.2 M solution of pentafluorophenol (PFP, 1.4 mg, 7.3 μmol) and N,N'-diisopropylcarbodiimide (DIC, 1.1 μl, 7.3 μmol) in $CH_2Cl_2$ at 0° C. The solution was allowed to reach room temperature and stirred for 4 h. Afterwards, the solvent was removed under reduced pressure. EtOAc (1 ml) was added to the mixture and the resulting suspension was suction filtered, to afford the desired activated acid in the filtrate. The EtOAc was removed under reduced pressure; DMF (0.5 ml) was added, followed by the hydrochloride salt of tubuphenylalanine methyl ester (25 mg, 98.4 μmol) and diisopropylethylamine (17 μl, 98.4 μmol). The mixture was stirred overnight at room temperature and DMF was then removed under reduced pressure. Purification of the crude product on reverse phase HPLC afforded 15 mg (19 μmol, 58% yield overall) of the methyl ester 5. $^1$H-NMR (599.8 MHz, $CDCl_3$): δ=0.83-0.90 (m, 6H), 0.94 (t, 3H, J=7.0 Hz), 0.98 (d, 3H, J=6.60 Hz), 1.07 (d, 3H, J=6.2 Hz), 1.15 (d, 3H, J=7.0 Hz), 1.22 (m, 1H), 1.34-1.42 (m, 5H), 1.54-1.81 (m, 8H), 2.0-2.10 (m, 5H), 2.20-2.35 (m, 2H), 2.58-2.64 (m, 1H) 2.74-2.80 (br m, 1H), 2.85-2.89 (m, 1H), 2.98-3.01 (m, 1H), 3.05-3.10 (m, 1H), 3.21-3.25 (m, 1H), 3.35 (m, 1H), 3.62 (s, 3H), 3.72-3.77 (m, 1H), 4.30 (m, 1H), 4.39 (m, 1H), 4.55-4.67 (br m, 2H), 5.09-5.19 (m, 1H), 7.07 (m, 1H), 7.21 (m, 1H), 7.25 (m, 4H), 7.37 (m, 1H), 7.96 (s, 1H) ppm. HRMS calcd for $C_{42}H_{67}N_6O_7S$ $[M+H]^+$: 799.4786. found: 799.4786.

Compound 6

Silyl ether 3 (17 mg, 24 μmol) was submitted first to acid hydrolysis followed by cleavage of the ethyl ester and coupling with the hydrochloride salt of tubuphenylalanine methyl ester (15 mg, 60 μmol) in a similar way described for the synthesis of compound 5. Purification of the crude product on reverse phase HPLC rendered 10 mg (13 μmol, 55% yield overall) of the methyl ester 6. $^1$H-NMR (599.8 MHz, CDCl$_3$): δ=0.95-0.99 (m, 9H), 1.06 (d, 3H, J=7.0 Hz), 1.08 (d, 3H, J=6.6 Hz), 1.09 (d, 3H, J=6.6 Hz), 1.15 (d, 3H, J=7.8 Hz), 1.18 (m, 1H), 1.43-1.50 (m, 1H), 1.54-1.72 (m, 6H), 1.79-1.82 (m, 2H), 1.97-2.03 (m, 3H), 2.06-2.12 (m, 2H), 2.25 (s, 3H), 2.51-2.53 (m, 1H), 2.58-2.64 (m, 1H), 2.85-2.88 (m, 1H), 2.93-2.95 (m, 1H), 2.97-3.01 (m, 1H), 3.62 (s, 3H), 3.75-3.79 (m, 1H), 3.93-3.98 (m, 1H), 4.29 (br m, 1H), 4.38 (m, 1H), 4.53 (m, 1H), 4.60 (d, 1H, J=10.6 Hz), 5.18 (m, 1H), 7.0 (m, 1H), 7.21 (m, 1H), 7.25 (m, 4H), 7.34 (m, 1H), 7.95 (s, 1H) ppm. HRMS calcd for C$_{41}$H$_{65}$N$_6$O$_7$S [M+H]$^+$: 785.4630. found: 785.4630.

Diastereomeric mixture 7

The diastereomeric mixture 4 (16 mg, 22 μmol) was submitted first to acid hydrolysis followed by cleavage of the ethyl ester and coupling with the hydrochloride salt of tubuphenylalanine methyl ester (14 mg, 0.055 mmol) in a similar way described for the synthesis of compound 5. Purification of the crude product on reverse phase HPLC rendered 22 mg (54 μmol, 62% yield over the three steps) of the methyl esters 7. As expected, the mixture of diasteromers is clearly visible by NMR (estimated ratio 1:1). Assigned signals belong to the whole mixture. $^1$H-NMR (599.8 MHz, CDCl$_3$): δ=0.82 (t, 3H, J=7.3 Hz), 0.90 (t, 6H, J=7.0 Hz), 0.93-0.96 (m, 9H), 1.02 (d, 3H, J=7.0 Hz), 1.04 (d, 3H, J=7.0 Hz), 1.08 (d, 6H, J=7.0 Hz), 1.12-1.14 (m, 6H), 1.15-1.19 (m, 2H), 1.36-1.42 (m, 10H), 1.49-1.70 (m, 16H), 1.74-1.88 (m, 6H), 1.94-2.06 (m, 6H), 2.23 (s, 3H), 2.26 (m, 2H), 2.29 (s, 3H), 2.36-2.40 (m, 2H), 2.53-2.62 (m, 2H), 2.83-2.92 (m, 4H), 2.95-3.01 (br m, 2H), 3.06-3.20 (m, 4H), 3.26 (m, 2H), 3.56 (s, 3H), 3.61 (s, 3H), 3.88-4.01 (m, 2H), 4.27-4.44 (m, 4H), 5.03 (m, 2H), 5.11 (m, 1H), 5.21 (m, 1H), 7.15 (m, 2H), 7.25 (m, 8H), 7.99 (s, 1H), 8.04 (s, 1H) ppm. HRMS calcd for C$_{43}$H$_{69}$N$_6$O$_7$S [M+H]$^+$: 813.4943. found: 813.4941.

General Procedure for Tubugis A, B and D:

Tubugi A

LiOH (1.4 mg, 57 μmol, 7.5 eq.) was added to a solution of the methyl ester 5 (6.1 mg, 7.6 μmol) in THF/H$_2$O (1 ml, 2:1, v/v) at 0° C. The reaction mixture was allowed to reach room temperature, stirred over 5 days, and acidified with aqueous 10% NaHSO$_4$ to pH 4. The mixture was then diluted with EtOAc (2 ml), the layers were separated and the aqueous phase was extracted with EtOAc (3×2 ml). The combined organic phases were concentrated under reduced pressure. The residue was then dissolved in 1 ml of pyridine and the solution was cooled to 0° C. Acetic anhydride (5.8 μl, 61 μmol) was added and the reaction was allowed to reach rt, stirred overnight and cooled to 0° C. Afterwards, 1 ml of H$_2$O was added. The stirring was kept for an additional 30 min and the solvent was then removed under reduced pressure. Purification of the crude product on preparative reverse phase HPLC rendered 5.1 mg (6.2 μmol, 82% overall yield) of tubugi A as a pail yellow solid. $^1$H-NMR (599.8 MHz, CD$_3$OD): Tup δ=1.16 (d, 3H, J=7.7 Hz, CH$_3$-10), 1.64 (m, 1H, CH$_b$-3), 1.99 (m, 1H, CH$_a$-3), 2.53 (m, 1H, CH-2), 2.87 (dd, 1H, J=13.5/6.6 Hz, CH$_b$-5), 2.91 (dd, 1H, J=13.5/7.3 Hz, CH$_a$-5), 4.36 (m, 1H, CH-4), 7.15 (m, 2H, CH-9), 7.22 (m, 2H, CH-7, CH-7'), 7.22 (m, 2H, CH-8, CH-8') ppm. Tuv δ=0.78 (d, 3H, J=6.6 Hz, CH$_3$-10)$^{a)}$, 0.86 (t, 3H, J=7.4 Hz, CH$_3$-16), 1.07 (d, 3H, J=6.5 Hz, CH$_3$-9)$^{a)}$, 1.31 (m, 2H, CH$_3$-15), 1.42 (m, 2H, CH$_2$-14), 1.78 (m, 1H, CH-8), 1.92 (m, 1H, CH$_b$-6), 2.33 (ddd, 1H, J=15.1/13.6/11.5 Hz, CH$_a$-6), 2.15 (s, 3H, CH$_3$CO), 3.11 (dt, 1H, J=13.5/7.0 Hz, CH$_b$-13), 3.24 (dt, 1H, J=13.5/7.0 Hz, CH$_a$-13), 3.79 (d, 1H, J=17.7 Hz, CH$_b$-11), 4.58 (br s, 1H, CH-7), 4.75 (d, 1H, J=17.7 Hz, CH$_a$-11), 6.31 (dd, 1H, J=11.5/1.9 Hz, CH-5), 8.05 (s, 1H, CH-3) ppm. L-Ile δ=0.88 (t, 3H, J=7.4 Hz, CH$_3$-5), 0.98 (d, 3H, J=6.8 Hz, CH$_3$-6), 1.14 (m, 1H, CH$_b$-4), 1.57 (m, 1H, CH$_a$-4), 2.0 (m, 1H, CH-3), 4.43 (d, 1H, J=9.3 Hz, CH-2) ppm. D-Mep δ=1.36 (m, 1H, CH$_b$-4), 1.59 (m, 1H, CH$_b$-3), 1.61 (m, 1H, CH$_b$-5), 1.70 (m, 1H, CH$_a$-5), 1.80 (m, 1H, CH$_a$-4), 1.85 (m, 1H, CH$_a$-3), 2.26 (m, 1H, CH$_b$-6), 2.28 (s, 3H, CH$_3$-7), 2.78 (br d, 1H, J=10.9 Hz, CH-2), 3.03 (br d, 1H, J=7.4 Hz, CH$_a$-6) ppm. HRMS calcd for C$_{43}$H$_{67}$N$_6$O$_8$S [M+H]$^+$: 827.4735. found: 827.4746 ($^a$=interchangeable assignment).

Tubugi B

The methyl ester 6 (4.9 mg, 6.3 µmol) was submitted to basic hydrolysis followed by acetylation of the secondary alcohol in a similar way as described for the synthesis of tubugi A to render 4.4 mg (5.4 µmol, 86% overall yield) of the tubugi B as a yellow solid after purification on preparative reverse phase HPLC. $^1$H-NMR (599.8 MHz, CD$_3$OD): δ=0.80 (d, 3H, J=6.6 Hz), 0.90 (t, 3H, J=7.3 Hz), 1.0 (d, 6H, J=6.6 Hz), 1.07 (d, 3H, J=6.6 Hz), 1.14 (m, 1H), 1.17 (d, 3H, J=6.6 Hz), 1.18 (d, 3H, J=7.0 Hz), 1.42-1.45 (m, 1H), 1.57-1.61 (m, 2H), 1.63-1.69 (m, 3H), 1.77-1.86 (m, 3H), 1.95 (m, 1H), 2.02 (m, 2H), 2.16 (s, 3H), 2.32-2.37 (m, 2H), 2.43 (s, 3H), 2.49-2.56 (m, 1H), 2.85-2.94 (m, 2H), 3.06 (m, 1H), 3.16 (m, 1H), 3.78 (d, 1H, J=17.9 Hz), 3.96 (m, 1H), 4.37 (m, 1H), 4.44 (d, 1H, J=9.8 Hz), 4.57 (br m, 1H), 4.70 (d, 1H, J=17.6 Hz), 6.31 (dd, 1H, J=11.4/1.8 Hz), 7.17 (m, 1H), 7.23 (m, 4H), 8.07 (s, 1H) ppm. HRMS calcd for C$_{42}$H$_{65}$N$_6$O$_8$S [M+H]$^+$: 813.4579. found: 813.4585.

The mixture of compounds 7 (8.6 mg, 10.6 µmol) was submitted first to basic hydrolysis followed by acetylation of the secondary alcohol (catalytic amounts of DMAP were added) in a similar way as described for the synthesis of tubugi A to afford 6.3 mg (7.5 µmol, 71% overall yield) of tubugi D as a mixture of diastereomers after purification on preparative reverse phase HPLC. Two conformers of each diastereomer can be distinguished by NMR. Assigned signals belong to the whole mixture. $^1$H-NMR (599.8 MHz, CD$_3$OD): δ=0.87-0.95 (m, 36H), 0.97-1.07 (m, 24H), 1.12-1.17 (m, 16H), 1.27-1.39 (m, 12H), 1.44-1.52 (m, 8H), 1.57-1.77 (m, 40H), 1.82-1.95 (m, 8H), 1.96-2.07 (m, 8H), 2.13 (s, 3H), 2.16 (s, 3H), 2.20 (s, 3H), 2.24 (s, 3H), 2.26-2.35 (m, 8H), 2.50-2.60 (m, 16H), 2.86-2.96 (m, 12H), 3.10-3.27 (m, 12H), 3.95-4.01 (m, 4H), 4.35 (m, 8H), 6.05 (m, 2H), 6.26 (dd, 2H, J=10.6/2.2 Hz), 7.14 (m, 4H), 7.22 (m, 16H), 8.02 (s, 1H), 8.05 (s, 1H), 8.06 (s, 1H), 8.10 (s, 1H) ppm. HRMS calcd for C$_{44}$H$_{69}$N$_6$O$_8$S [M+H]$^+$: 841.4892. found: 841.4879.

The biological activity of tubugis A, B and D was evaluated against human cancer cell lines, using tubulysin A and taxol as reference compounds. As shown in Table 1, tubugis A, B and D showed a prominent biological profile with a cytotoxic activity almost identical to that of tubulysin A (small differences within the error limits of the experiment).

TABLE 1

| Cytotoxic activity (GI$_{50}$ Values [nM]) | | |
|---|---|---|
| Compound | PC-3 | HT-29 |
| tubulysin A | 0.21 | 0.32 |
| tubugi A | 0.23 | 0.14 |
| tubugi B | 0.29 | 0.34 |
| tubugi D | 0.22 | 0.56 |
| taxol | 7.2 | 5.3 |

Tubugi D (diastereomeric mixture)

Tubugi H (Diastereomeric Mixture)

Free amine generated in situ

Armstrong isocyanide key intermediate 8 tubugi H

Peptoid 9

N-Boc tubuvaline ethyl ester (74 mg, 0.20 mmol) was dissolved in $CH_2Cl_2$/TFA (3 mL, 4:1, v/v). The mixture was stirred 1 h at room temperature and afterward concentrated under reduced pressure. The resulting oil was redissolved in $CH_2Cl_2$ and the solution was washed with saturated aqueous $NaHCO_3$ (3×5 mL) and brine (3×5 mL). The layers were separated and the organic phase was dried over $Na_2SO_4$, filtered, and the solvent removed under reduced pressure. The crude material was used in the next step without further purification.

To a solution of the free amine obtained above in MeOH (3 mL) was slowly added a suspension of formaldehyde (6.0 mg, 0.20 mmol) in MeOH (3 mL) using a syringe pump over a period of 2 h. Subsequently, Mep-Ileu-OH (112 mg, 0.44 mmol) was added, the reaction was stirred 10 min and afterward a solution of Armstrong isocyanide (21 mg, 0.20 mmol) in MeOH (3 mL) was added over a period of 3 h using a syringe pump. The reaction mixture was stirred for an additional 48 h and the solvent was then removed under reduced pressure. Flash column chromatography (gradient: $CH_2Cl_2$/MeOH/$Et_3N$, 30:1:0.3, v/v/v→$CH_2Cl_2$/MeOH/$Et_3N$, 15:1:0.3, v/v/v) afforded a mixture of compounds containing the key intermediate 8. HRMS calculated for $C_{33}H_{54}N_5O_6S$ $[M+H]^+$: 648.3789. found: 648.3787 and HRMS calculated for $C_{28}H_{43}N_4O_5S$ $[M+H]^+$: 547.2949. found: 547.2953. Several attempts to purify this mixture either by flash column chromatography resulted unsuccessful. Thus, the mixture was dissolved in THF/$H_2O$ (2 mL, 2:1, v/v) and LiOH (11.9 mg, 0.49 mmol) was added at 0° C. The reaction mixture was stirred 6 h and allowed to reach gradually rt. Hereafter it was acidified with 37% HCl aqueous solution until pH=7-8 and then slightly acidified until pH=6.8 with aqueous buffer solution, i.e., by dilution of the mixture with the buffer solution). The mixture was extracted with n-butanol (3×20 mL), the layers were separated and the combined organic phases were concentrated under reduced pressure to afford a crude material which was used in the next step without any additional purification.

The acid obtained above was coupled with the hydrochloride salt of tubuphenylalanine (Tup) methyl ester (22.5 mg, 0.09 mmol) following the DIC/PFP protocol in a similar way as described for the synthesis of compound 5 to give after reverse phase HPLC purification the peptoid 9 (8.0 mg, 9.8 μmol). HRMS calculated for $C_{44}H_{67}N_6O_7S$ $[M+H]^+$: 823.4795. found: 823.4789. Subsequently, the obtained oil was dissolved in a commercially available 4 N solution of HCl in dioxane (2 mL) and the mixture was stirred for 1 h. Afterward, MeOH (2 mL) was added and the stirring was continued for an additional 3 h. (The hydrolysis of the convertible Ugi-Armstrong-amides alternatively can also be performed on the stage of intermediates like 8 etc.). The solvent was removed under reduced pressure and the residue was dissolved in pyridine (4.0 mL) and the solution was cooled to 0° C. Acetic anhydride (84 μL, 0.90 mmol) was added and the reaction was stirred overnight and allowed to reach gradually rt. The solvent was removed under reduced pressure and the crude mixture submitted to reverse phase HPLC purification to render 6.3 mg of tubugi H (7.9 μmol, 4.0% yield overall). $^1$H-NMR (599.8 MHz, $CD_3OD$, representative signals): δ=0.79 (d, 3H, J=6.6 Hz), 0.90 (t, 3H, J=7.4 Hz), 0.98 (d, 3H, J=7.0 Hz), 1.01 (d, 3H, J=6.6 Hz), 1.14 (d, 3H, J=7.4 Hz), 1.18-1.23 (m, 1H), 1.38 (m, 1H), 2.16 (s, 3H), 2.41 (s, 3H), 3.59 (s, 3H), 3.61 (s, 3H), 3.63 (d, 1H), 4.35 (m, 1H), 4.42 (d, 1H, J=9.9 Hz), 4.58 (br m, 1H), 4.83 (overlap signal), 6.32 (dd, 1H, J=11.6/1.9 Hz), 7.16 (m, 1H), 7.21 (m, 4H), 8.01 (s, 1H) ppm. HRMS calculated for $C_{41}H_{62}N_5O_9S$ $[M+H]^+$: 800.4277. found: 800.4280.

In summary, the present invention provides a concise and reliable synthesis of a new class of cytotoxic tubulysin analogues (tubugis) with $GI_{50}$ values in the nanomolar and high picomolar range. The rare and labile N,O-acetal functionality which is present on the most active natural tubulysins has been replaced by a much more stable tert-peptide backbone with retention or even improvement of the cytotoxic activity.

The invention claimed is:
1. Tubulysin compounds having the general formula (II)

(II)

wherein:
W is a group selected from $OR^{13}$ or $NR^{14}R^{15}$,
X is a substituted five- or six-membered aromatic (arylene) or heteroaromatic ring (hetero-arylene),
Y is H, —$CH_2$—, NH, NMe, a sulfur atom or an oxygen atom,
Z is a group selected from the group consisting of $OR^{16}$, $NR^{17}R^{18}$, wherein
$R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$, $R^{18}$, $R^{20}$, $R^{21}$, $R^{23}$, $R^{24}$ and $R^{25}$ each independently represents H, a substituted or unsubstituted alkyl, a substituted or unsubstituted cycloalkyl, a substituted or unsubstituted aryl, a substituted or unsubstituted heteroaryl, or a substituted or unsubstituted heteroalkyl, and where $R^1$ and $R^3$ or $R^1$ and $R^2$ may be linked to form together with the nitrogen atom a five-membered pyrrolidine ring or a six-membered piperidine ring, $R^{12}$ is H, H an acyl group (C(O)R), a substituted or unsubstituted alkyl, a substituted or unsubstituted cycloalkyl, or a substituted or unsubstituted aryl, with R being a substituted or unsubstituted alkyl, a substituted or unsubstituted cycloalkyl, or a substituted or unsubstituted aryl, $R^{19}$ represents H, halogen, nitro, amine, monoalkylamine or dialkylamine group, hydroxyl, alkyloxy, a substituted or unsubstituted alkyl, a substituted or unsubstituted cycloalkyl, a substituted or unsubstituted aryl, a substituted or unsubstituted heteroaryl, or a substituted or unsubstituted heteroalkyl; in positions 2 and/or 3 and/or 4, and/or 5, and/or 6, or in any combination thereof, $R^{22}$ represents OH, $NH_2$, alkyloxy, alkylamino or dialkylamino group, or a linker, V is a sulfur or oxygen atom, —$CH_2$—, NH or NH-alkyl group, and pharmaceutical acceptable salts, hydrates, solvates, prodrugs, metabolites, stereoisomers, stereoisomeric mixtures, and polymorphs thereof.

2. The tubulysin compounds according to claim 1, wherein Y is an oxygen atom and X is a thiazole or an oxazole.

3. The tubulysin compounds according to claim 1, wherein $R^1$ and $R^3$ are linked to form a piperidine moiety.

4. The tubulysin compounds according to claim 1, wherein Z is tubuphenylalanyl (Tup).

5. The tubulysin compounds according to claim 1, wherein W is $NR^{14}R^{15}$.

6. The tubulysin compounds according to claim 1 having the general formula (III):

(III)

wherein:
R' is H or a methyl group,
$R^{14}$, $R^{15}$ and Z are defined as above.

7. The tubulysin compounds according to claim 1, wherein the compounds are selected from the group consisting of 8. The tubulysin compounds according to claim 1, wherein the compounds are conjugated to
   (i) biomolecules for the target-oriented delivery, or
   (ii) molecular moieties, which can improve their solubility, penetration, detection, release or selectivity.

9. The tubulysin compounds according to claim 8, wherein the biomolecule is a peptide, functional protein, enzyme, antigen, antibody, (oligo)saccharide, (poly)saccharide, nucleic acid, hormone or hormone receptor binder, or vitamin.

10. The tubulysin compounds according to claim 8, wherein the molecular moieties are selected from polyethyleneglycols, polyamines, polyguanidines, dyes, receptor ligands, or polymers.

11. A pharmaceutical formulation comprising one or more of the tubulysin compounds according to claim 1 and one or more pharmaceutically acceptable carriers, adjuvants and/or diluents.

12. A method for the treatment of proliferative disorders comprising administering a tubulysin compounds according to claim 1.

13. A method of producing compounds having the general formula (IV) by an Ugi-type reaction for the generation of the tertiary amide bond, as shown below -continued (IV)

wherein:
- X is a substituted five- or six-membered aromatic (arylene) or heteroaromatic ring (heteroarylene),
- Y is H, —CH$_2$—, NH, NMe, a sulfur atom or an oxygen atom,
- Z is a group selected from the group consisting of OR$^{16}$, NR$^{17}$R$^{18}$, -continued wherein R$^1$, R$^2$, R$^3$, R$^4$, R$^5$, R$^6$, R$^7$, R$^8$, R$^9$, R$^{10}$, R$^{11}$, R$^{17}$, R$^{18}$, R$^{20}$, R$^{21}$, R$^{23}$, R$^{24}$ and R$^{25}$ each independently represents H, a substituted or unsubstituted alkyl, a substituted or unsubstituted cycloalkyl, a substituted or unsubstituted aryl, a substituted or unsubstituted heteroaryl, or a substituted or unsubstituted heteroalkyl, and where R$^1$ and R$^3$ or R$^1$ and R$^2$ may be linked to form together with the nitrogen atom a five-membered pyrrolidine ring or a six-membered piperidine ring, R$^{12}$ is H, H an acyl group (C(O)R), a substituted or unsubstituted alkyl, a substituted or unsubstituted cycloalkyl, or a substituted or unsubstituted aryl, with R being a substituted or unsubstituted alkyl, a substituted or unsubstituted cycloalkyl, or a substituted or unsubstituted aryl, R$^{14}$, R$^{16}$ is a substituted or unsubstituted alkyl, a substituted or unsubstituted cycloalkyl, a substituted or unsubstituted aryl, a substituted or unsubstituted heteroaryl, a substituted or unsubstituted heteroalkyl, or a usual O-protective group, R$^{19}$ represents H, halogen, nitro, amine, monoalkylamine or dialkylamine group, hydroxyl, alkyloxy, a substituted or unsubstituted alkyl, a substituted or unsubstituted cycloalkyl, a substituted or unsubstituted aryl, a substituted or unsubstituted heteroaryl, or a substituted or unsubstituted heteroalkyl; in positions 2 and/or 3 and/or 4, and/or 5, and/or 6; or in any combination thereof, R$^{22}$ represents NH$_2$, alkyloxy, alkylamino or dialkylamino group, or a linker, and V is a sulfur or oxygen atom, —CH$_2$—, NH or NH-alkyl group.

* * * * *